(12) United States Patent
Bacher et al.

(10) Patent No.: US 8,231,622 B2
(45) Date of Patent: Jul. 31, 2012

(54) BIPOLAR COAGULATION INSTRUMENT

(75) Inventors: Uwe Bacher, Tuttlingen (DE); Rainer Hermle, Gosheim (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 12/847,551

(22) Filed: Jul. 30, 2010

(65) Prior Publication Data

US 2011/0022048 A1    Jan. 27, 2011

Related U.S. Application Data

(63) Continuation of application No. PCT/EP2009/000344, filed on Jan. 21, 2009.

(30) Foreign Application Priority Data

Jan. 31, 2008    (DE) .................. 10 2008 006 880

(51) Int. Cl.
*A61B 18/14*    (2006.01)
(52) U.S. Cl. ........................................ 606/50
(58) Field of Classification Search ............ 606/45, 606/48–50; 604/35
See application file for complete search history.

(56) References Cited

U.S. PATENT DOCUMENTS

| | | | | |
|---|---|---|---|---|
| 3,828,780 A | * | 8/1974 | Morrison, Jr. .................. | 604/20 |
| 5,084,045 A | * | 1/1992 | Helenowski ................... | 606/32 |
| 5,738,648 A | * | 4/1998 | Lands et al. ................... | 604/35 |
| 5,814,044 A | * | 9/1998 | Hooven ......................... | 606/48 |
| 5,989,249 A | * | 11/1999 | Kirwan, Jr. ................... | 606/50 |
| 6,406,476 B1 | * | 6/2002 | Kirwan et al. ................. | 606/50 |

FOREIGN PATENT DOCUMENTS

| | | |
|---|---|---|
| DE | 4138115 A1 | 5/1993 |
| DE | 4439553 C1 | 4/1996 |
| DE | 19541566 A1 | 5/1997 |
| DE | 20117907 U1 | 1/2002 |
| DE | 102004033595 A1 | 2/2006 |
| GB | 2406057 A | 3/2005 |
| WO | 2006092563 A1 | 9/2006 |
| WO | 2006102124 A2 | 9/2006 |

OTHER PUBLICATIONS

International Search Report and Written Opinion of the International Searching Authority; PCT/EP2009/000344; Apr. 8, 2009; 9 pages.
International Preliminary Report on Patentability and Written Opinion of the International Searching Authority (translation); PCT/EP2009/000344; Sep. 7, 2010; 8 pages.

* cited by examiner

*Primary Examiner* — Lee Cohen
(74) *Attorney, Agent, or Firm* — St. Onge Steward Johnston & Reens LLC

(57) ABSTRACT

The invention relates to a bipolar coagulation instrument having a hollow shaft configured as a suction and/or flushing tube and having two electrodes that are electrically insulated with respect to one another and extend beyond the distal end of the shaft. To provide a bipolar coagulation instrument that is both of simple structure and ensures an effective suction/flushing capacity, it is proposed with the invention that the hollow shaft should consist of two electrically conductive tubes coaxially mounted on one another that are electrically insulated with respect to one another and from the outside, so that the tubes constitute the electrodes.

15 Claims, 6 Drawing Sheets

BIPOLAR COAGULATION INSTRUMENT

CROSS-REFERENCE TO RELATED APPLICATIONS

The present application is a continuation of pending International patent application PCT/EP2009/000344 filed on Jan. 21, 2009 which designates the United States and claims priority from German patent application No. 10 2008 006 880.2 filed on Jan. 31, 2008.

FIELD OF THE INVENTION

The invention relates to a bipolar coagulation instrument with a hollow shaft configured as a suction and/or flushing tube as well as with two electrodes that are insulated with respect to one another and extend beyond the distal end of the shaft.

BACKGROUND OF THE INVENTION

A generic bipolar coagulation instrument is known for instance from DE 44 39 553 C1. These types of bipolar coagulation instruments are used for instance in paranasal surgery in addition to coagulation treatment to close vessels by means of electrodes charged with current. The combination of a bipolar coagulation instrument and a suction and/or flushing instrument is advantageous because the blood issuing from opened vessels during operations impedes the view of the surgical area. In these cases it is required, first, to rinse out and/or to suction out the operation area before the vessels can be closed again by coagulation.

The disadvantage with the known bipolar coagulation instruments is that because of the current feeder cable leading to the electrodes positioned on the distal end of the shaft, the free cross-section of the hollow shaft that is available for suctioning and/or flushing is significantly reduced, so that the suction/flushing capacity of the known instruments is insufficient in cases of severe bleeding. In addition, the known instruments, particularly in the area of the electrodes, have a complex structure, consisting of many individual subcomponents, that makes installation difficult and expensive.

On this basis it is the object of the invention to provide a bipolar coagulation instrument of the aforementioned type, which is of simple structure and ensures an effective suction/flushing capacity.

SUMMARY OF THE INVENTION

The solution of this object according to the invention is characterized in that the hollow shaft consists of two electrically conductive tubes that are mounted coaxially on one another and are electrically insulated with respect to one another and from the exterior, so that the tubes constitute the electrodes.

As a result of the inventive configuration of the electrodes as electrically conductive tubes that are mounted together coaxially, it is possible for the first time to make the entire free cross-section of the hollow shaft available as a suction and/or flushing channel, because cabling is no longer necessary in the interior of the shaft. The insulation of the tubes with respect to one another and from the environment is achieved by the insulating layers that are positioned on the inner tube and the outer tube.

According to a practical embodiment of the invention it is proposed that the tubes should be electrically insulated with respect to one another and from the outside by the layers surrounding the tubes coaxially, so that two tubes and the two insulating layers advantageously are form-locked contiguous with one another in order to make possible an especially compact structure of the shaft.

To achieve an essentially fully flat and form-locked installation of the insulating layers on each of the tubes, it is proposed with the invention that the insulating layers should be configured as hoses, in particular shrink hoses, applied on the inner tube and the outer tube.

According to an alternative embodiment of the invention it is proposed that insulating layers should be configured as layers of a synthetic or ceramic material applied on the inner tube and the outer tube.

It is further proposed with the invention that to configure the actual working electrodes on the distal ends of the inner tube and the outer tube, tubular segments protruding like fingers should be configured that extend beyond the distal end of the shaft, so that these tubular segments protruding like fingers, advantageously opposite to one another, are positioned on the distal end of the shaft.

In order to ensure a form-locked positioning and gapless insulation of the insulating layers on the tubes in the area of the distal free ends of the tubes, it is further proposed with the invention that on the free ends of the tubes in the transition to the protruding electrode tips beveled surfaces should be configured which reduce the outer diameter of the tubes and taper diagonally inward.

To be able to regulate easily and quickly the suction capacity of the volume flow rate suctioned out through the hollow shaft, it is proposed with a particular embodiment of the invention that a throttle opening should be configured in the shaft that can be opened and closed with one finger by the operator of the inventive coagulation instrument. The throttle opening in this case is advantageously of such size that when the throttle opening is completely opened the suction capacity essentially comes to a halt.

To provide easy handling of the throttle opening, the invention foresees that the throttle opening is configured in the vicinity of a handle positioned on the proximal end of the shaft, so that the user can hold the instrument with just one hand while simultaneously operating the throttle opening.

With the inventive coagulation instrument, because both tubes that constitute the shaft are configured as electrically conductive electrodes, it is proposed according to a preferred embodiment of the invention that a recess should be configured surrounding the throttle opening at a distance on all sides in the area of the throttle opening in the outer tube, in order to prevent a short-circuit between the two electrodes in the area of the throttle opening.

To ensure flawless closing of the throttle opening by means of one of the instrument user's fingers, it is further proposed with the invention that a recess surrounding the throttle opening at a distance on all sides should also be configured in the insulating layer that is positioned on the outer tube.

Further characteristics and advantages of the invention can be seen from the appended drawings, in which one embodiment of an inventive bipolar coagulation instrument is illustrated only as an example, without restricting the invention to this embodiment.

DETAILED DESCRIPTION OF THE INVENTION

Figure 1:
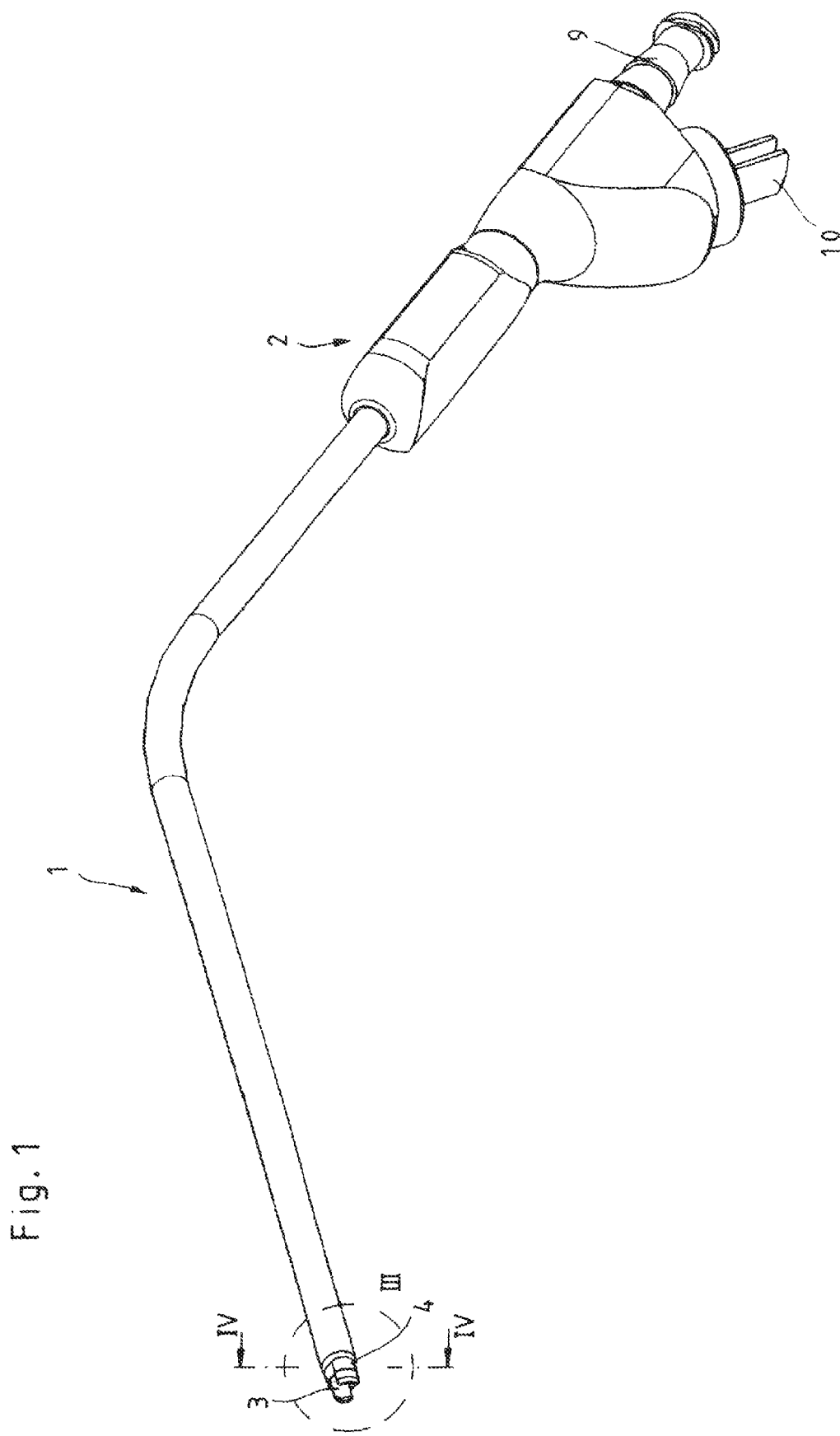
FIG. 1 shows a perspective side view of an inventive bipolar coagulation instrument.
Figure 2:
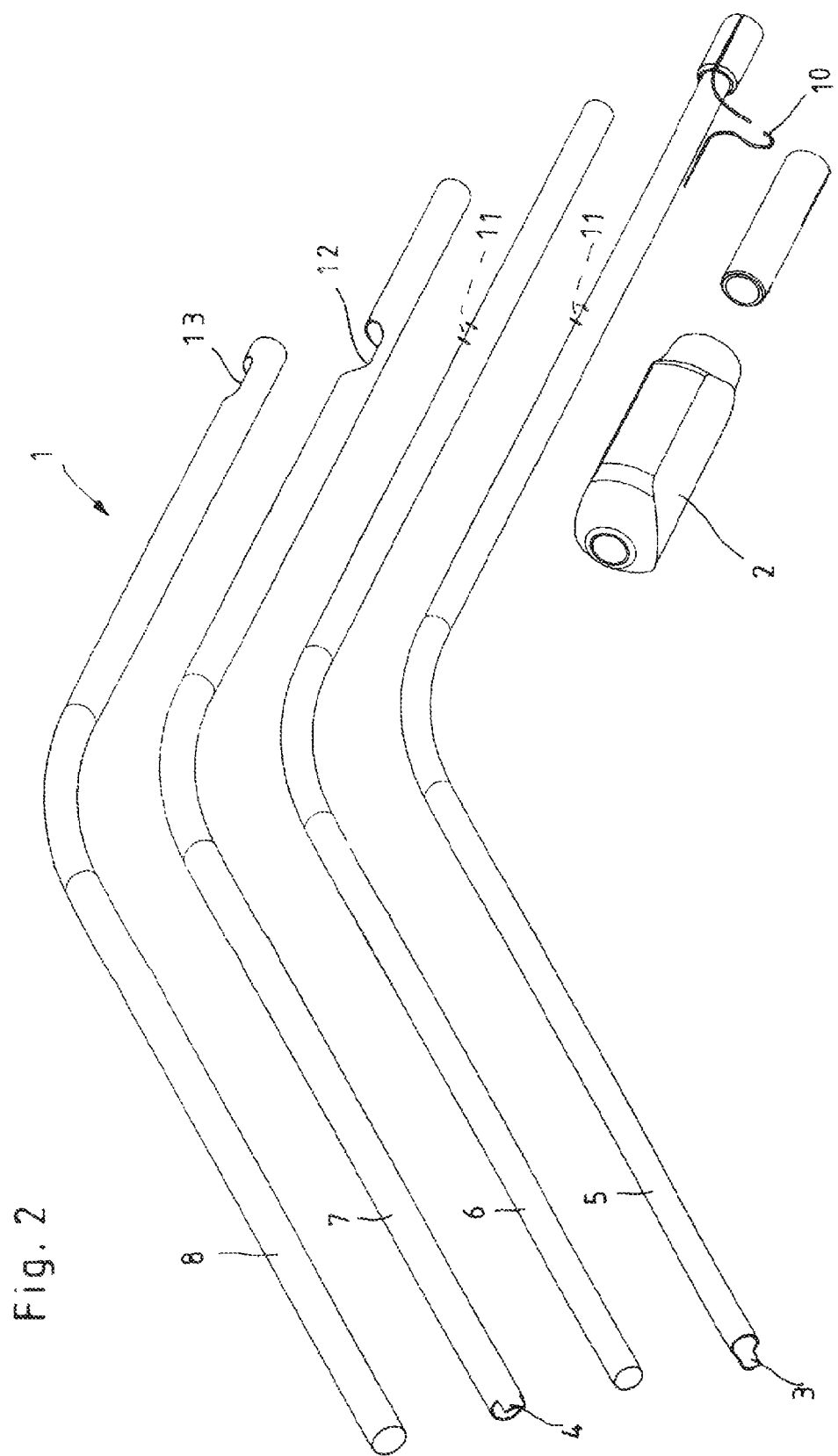
FIG. 2 shows an exploded sketch of the instrument according to
FIG. 1.

The medical bipolar coagulation instrument, as shown especially in FIGS. 1 and 2, consists essentially of a hollow shaft 1 configured as a suction/flushing channel, a handle 2 mounted on the proximal end of the shaft 1, and two electrode tips 3 and 4 that extend beyond the hollow shaft 1 on the distal end.

As can be seen in particular from FIG. 2, the hollow shaft 1 is configured in several layers consisting of an inner tube 5, an electrically insulating layer 6 that coaxially surrounds the inner tube 5, an outer tube 7 that coaxially surrounds the inner tube 5 as well as the insulating layer 6, and an electrically insulating layer 8 that coaxially surrounds the outer tube 7. In the illustrated embodiment the insulating layers 6 and 8, which on the one hand electrically insulate the tubes 5 and 7 with respect to one another and on the other hand electrically insulate the shaft 1 from the outside, are configured as shrink hoses that surround the tubes 5 and 7 in form-locked manner.

It is also possible of course to obtain the electrical insulation of the tubes 5 and 7 with respect to one another and from the environment also by means of other electrically insulating layers, such as by coating the tubes 5 and 7 with electrically insulating layers made of plastic or ceramic material.

Figure 3:
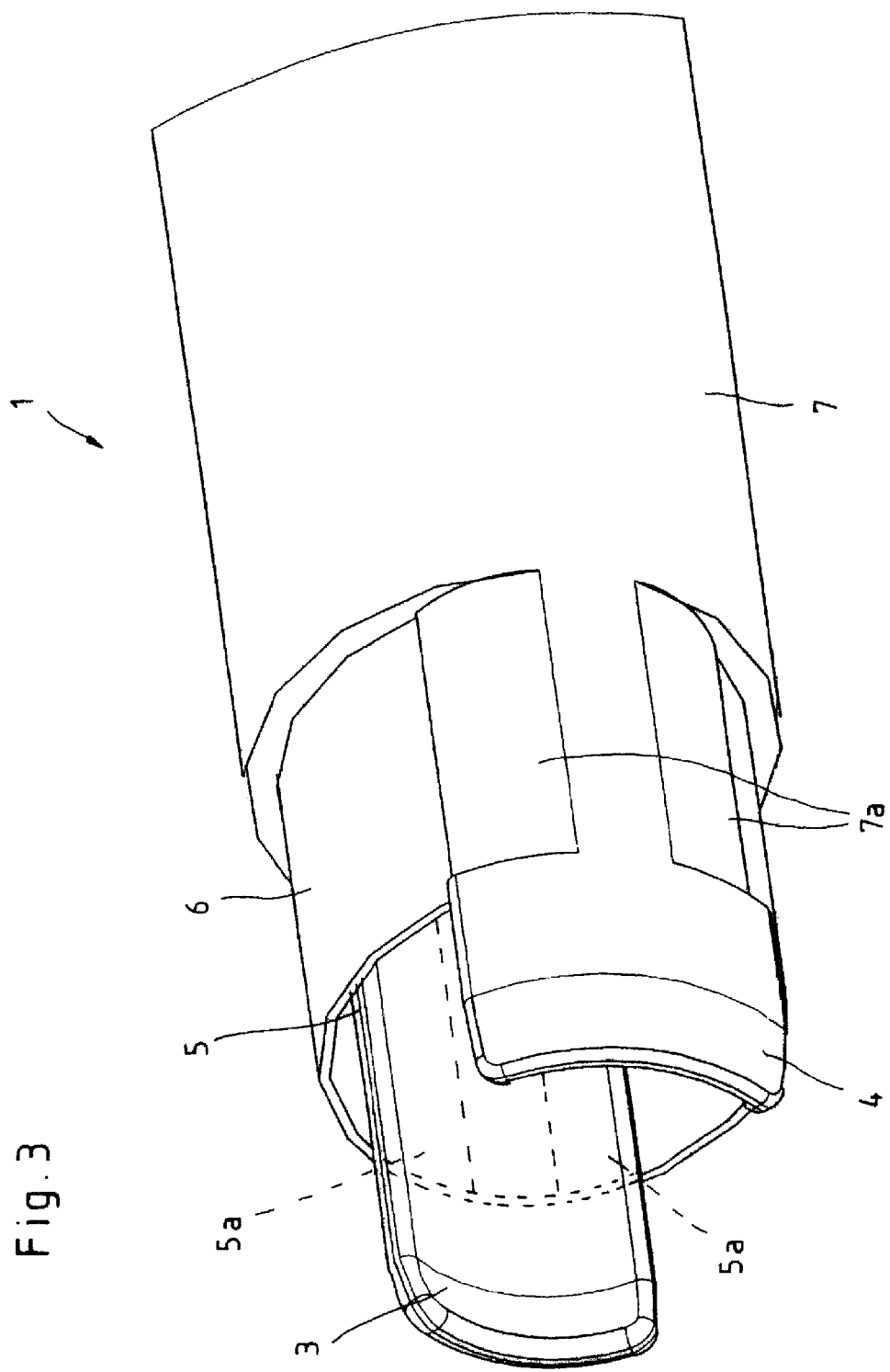
FIG. 3 shows a partially cut-out, enlarged illustration of detail III from FIG. 1.

The tubes 5 and 7, in turn, are at least partly electrically conductive in configuration, so that the tubes 5 and 7 simultaneously constitute the electrodes of the bipolar coagulation instrument. To configure the actual electrode tips 3 and 4, on the distal ends of the inner tube 5 and of the outer tube 7, tubular sections are configured, protruding in finger-like manner, which extend beyond the distal end of the shaft 1, as shown in FIGS. 1 and 3. These finger-like protruding electrode tips 3 and 4 are positioned opposite one another on the distal end of the shaft 1.

Figure 4:
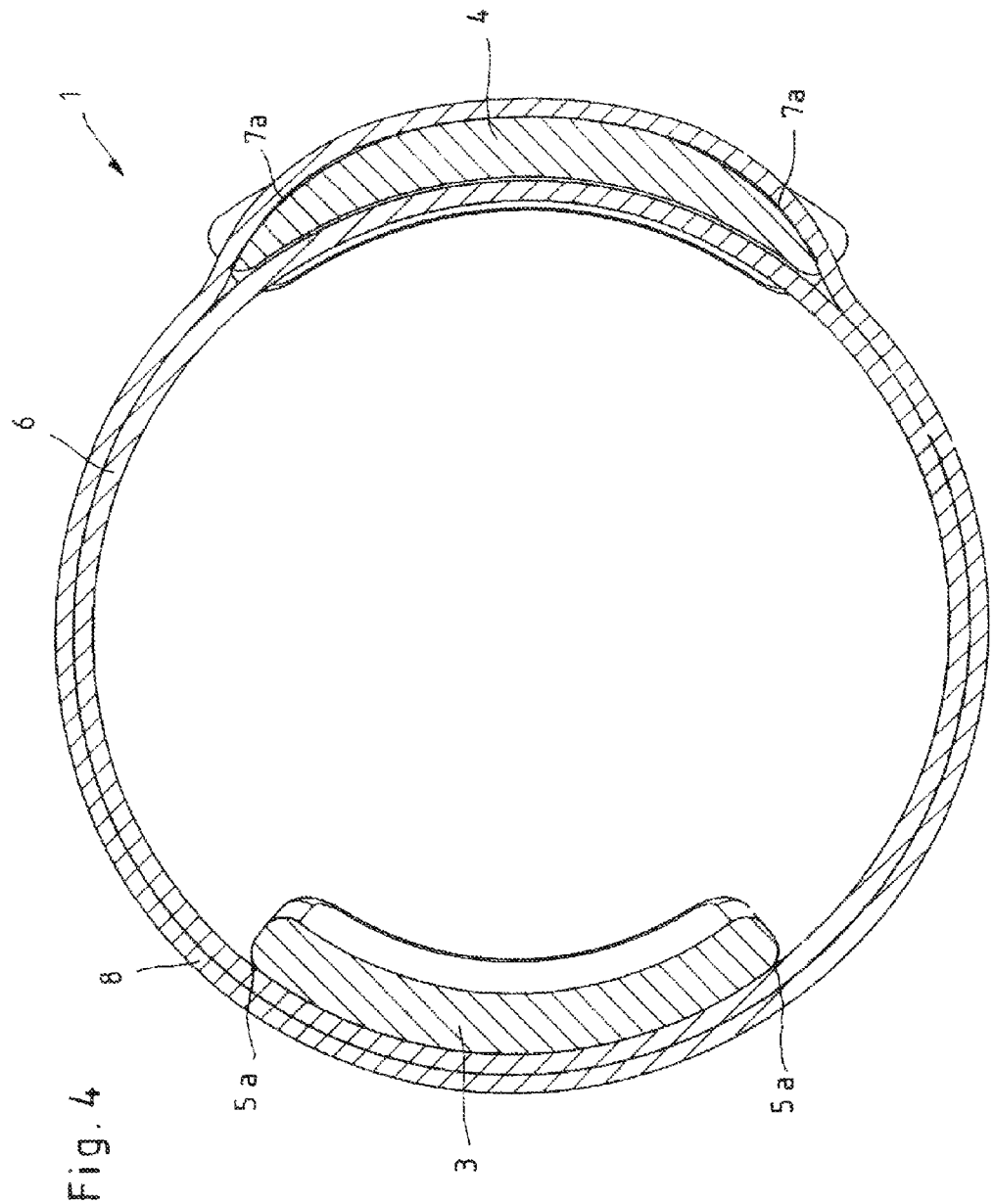
FIG. 4 shows a section along the line IV-IV from FIG. 1.

The multi-layered structure of the hollow shaft 1 can be seen both from the explosion drawing in FIG. 2 and in particular from FIGS. 3 and 4, which show the distal end of the shaft 1 that includes the electrode tips 3 and 4. The external insulating layer 8 has been omitted from FIG. 3 to allow a clearer view of the configuration of the electrode tips 3 and 4 as a distal extension of the tubes 5 and 7.

It can also be seen from FIGS. 3 and 4 how the tubes 5 and 7 are geometrically configured in the area of the transition to the electrode tips 3 and 4. To ensure a form-locked positioning and gapless insulation of the insulating layers 6 and 8 on the tubes 5 and 7 in the area of the distal free ends of the tubes 5 and 7, beveled surfaces 5a and 7a, inclined diagonally inward, are configured on the free ends of the tubes 5 and 7.

The configuration of the tubes 5 and 7, which constitute the hollow shaft 1, as electrodes of the bipolar coagulation instrument has the advantage that the entire free cross-section of the hollow shaft 1 is available as a suction and/or flushing channel and no cabling is required inside the shaft 1.

To configure the hollow shaft 1 as a suction and/or flushing channel, the handle 2 comprises on its proximal end a suction and/or flushing connection 9 for coupling to an external suction and/or flushing line.

The handle 2 in addition comprises a current connection 10 by which the tubes 5 and 7 configured as electrodes can be charged with current.

To make it possible for the operator to be able easily and quickly to regulate the suction capacity via the hollow shaft 1 configured as a suction and/or flushing channel, the hollow shaft 1 in the area of the handle 2 comprises a throttle opening 11 that connects the interior of the suction and/or flushing channel with the ambient air. In the illustrated embodiment the throttle opening 11 is configured as a borehole running essentially radially. Different-shaped throttle openings 11, such as oval, rectilinear, or similarly configured openings, are also possible of course.

Figure 5:
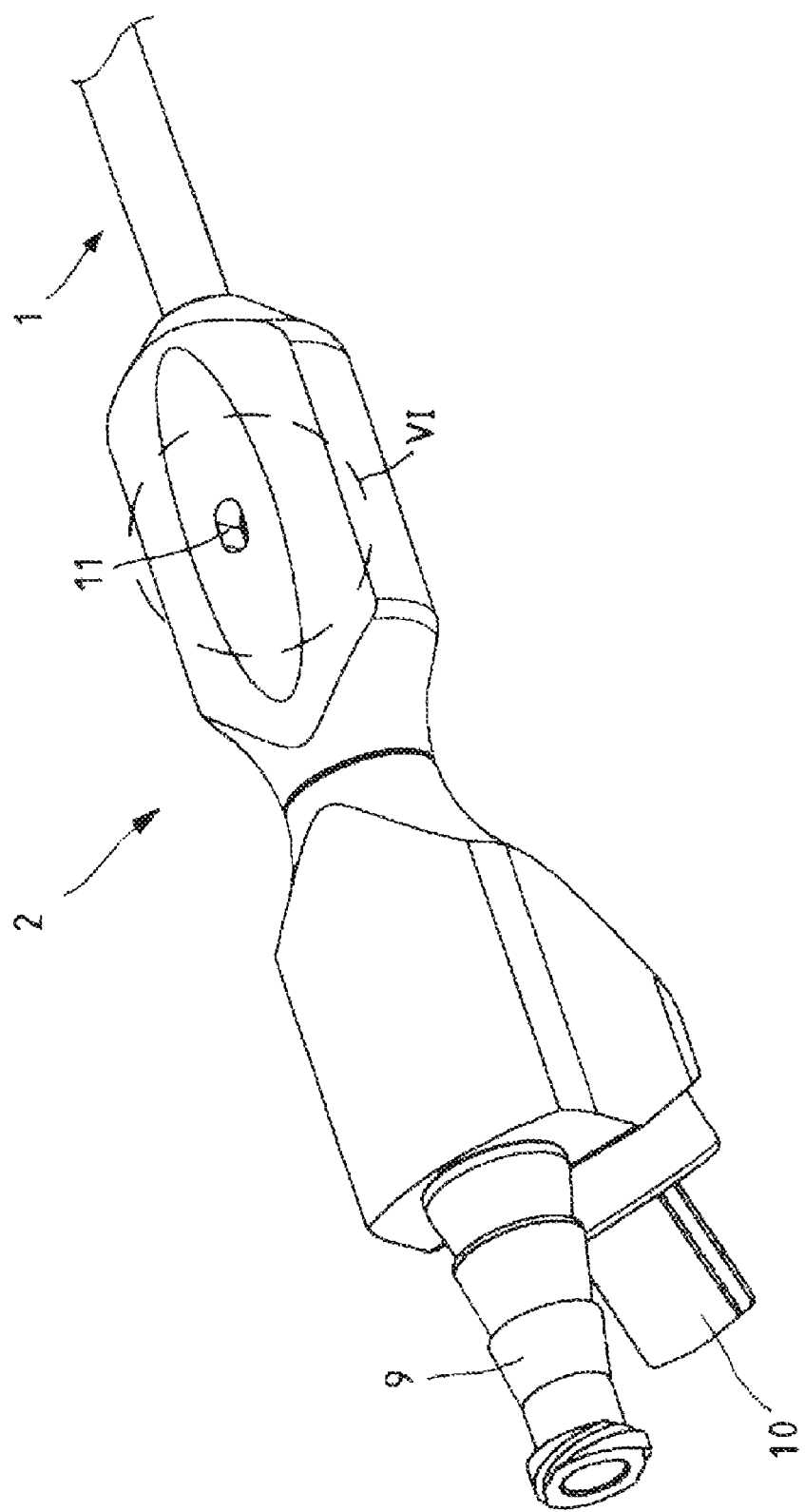
FIG. 5 shows an overhead view of the proximal end of the instrument from FIG. 1.
Figure 6:
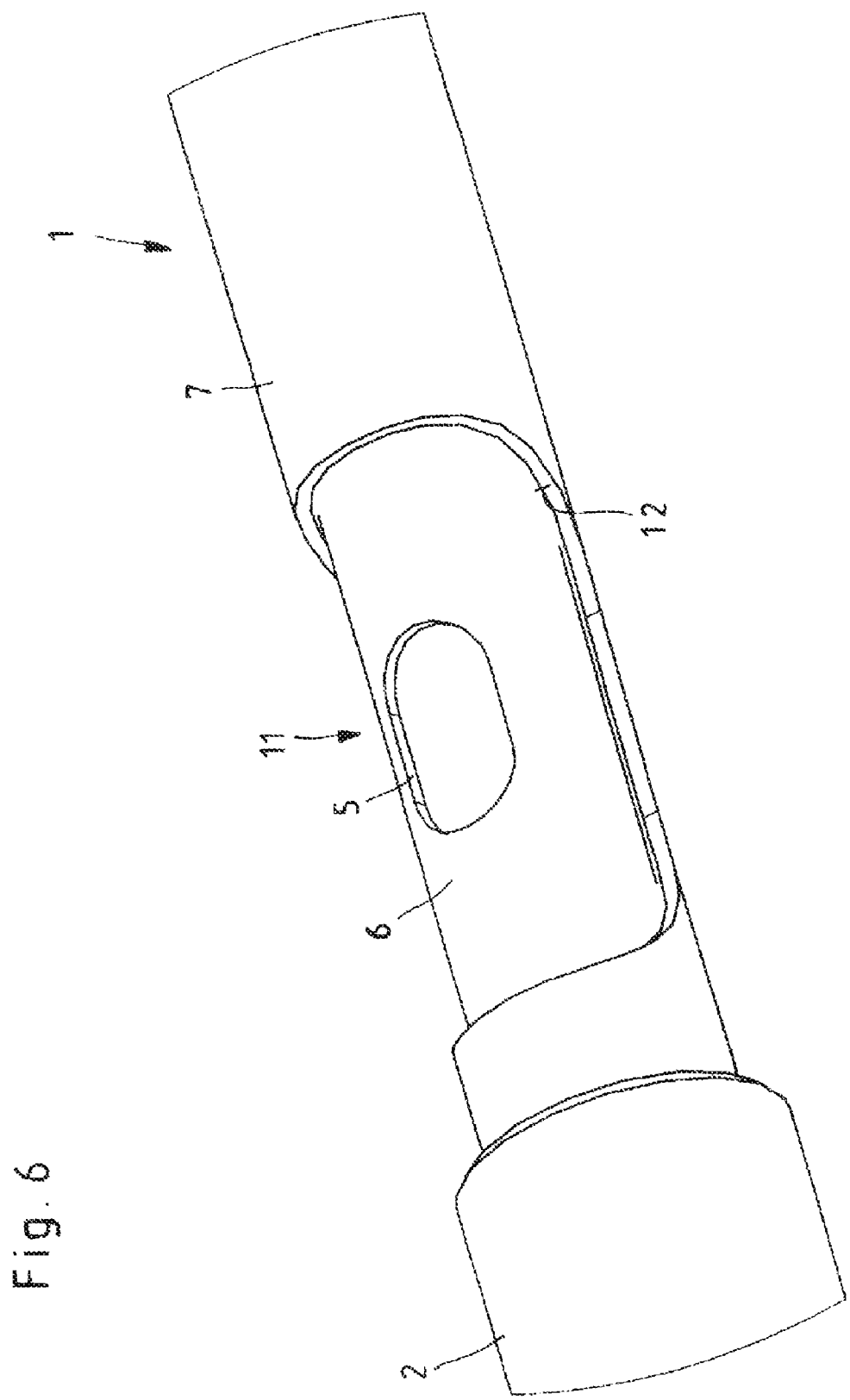
FIG. 6 shows a partially cut-out, enlarged illustration of detail VI from FIG. 5, but without handle.

As can be seen in particular from FIGS. 5 and 6, the throttle opening 11 is configured and placed on the handle in such a way that the operator can open and close the throttle 11 again with one finger, for instance with a finger of the hand that is also being used for holding the handle 2 to guide the instrument.

The throttle opening 11 here is advantageously of such dimensions that with the throttle opening 11 completely opened, the suction capacity essentially comes to a stop, because so much ambient air is drawn in by the opened throttle opening 11 that the suction capacity does not extend as far as the distal end of the shaft 1. The farther the operator closes the throttle opening 11 with a finger, the stronger becomes the suction capacity inside the hollow shaft and thereby the suction capacity from the operating area by way of the distal end of the shaft 1.

To prevent the eventuality in the area of the throttle opening 11 of a short-circuit between the tubes 5 and 7, which are constructed as electrodes, as a result of liquid or of shunting by the operator's finger, in the area of the throttle opening 11, in the outer tube 7, a recess 12 is configured surrounding the throttle opening 11 at a distance on all sides, for instance in the form of a clearance milling, as can be seen from FIG. 6, in which the outer insulating layer 8 has been omitted to allow better visibility.

As can be seen from FIG. 2, the outer insulating layer 8 in the area of the throttle opening 11 also comprises a recess 13 that surrounds the throttle opening 11 at a distance on all sides, in order to ensure complete closing of the throttle opening 11 by means of one of the operator's fingers.

A bipolar coagulation instrument as described above is differentiated in particular in that, on the one hand, it is composed in simple manner using only a few components and thus is configured so that it can be installed at reasonable price and, on the other hand, because of the configuration of the tubes 5 and 7, which constitute the hollow shaft 1, as electrodes of the bipolar coagulation instrument, the entire free cross-section of the hollow shaft 1 is available as a suction and/or flushing channel.

In addition, the configuration of the throttle opening 11 allows for easy, rapid, and effective regulation of the suction capacity in the interior of the hollow shaft 1, which is configured as a suction and/or flushing channel.

The invention claimed is:

1. A bipolar coagulation instrument having a hollow shaft configured as a suction and/or flushing tube and having two electrically insulated electrodes that are opposite one another and extend beyond a distal end of the shaft, whereby the hollow shaft consists of two at least partly electrically conductive tubes mounted coaxially on one another, which are insulated with respect to one another and to the outside, so that the tubes constitute the electrodes, wherein a throttle opening is configured in the shaft and a recess that surrounds the throttle opening at a distance on all sides is configured in the area of the throttle opening in the outer tube.

2. A bipolar coagulation instrument according to claim 1, wherein the tubes are electrically insulated with respect to one another and from the outside by two layers that coaxially surround the tubes.

3. A bipolar coagulation instrument according to claim 2, wherein the two tubes and the two insulating layers are form-locked together.

4. A bipolar coagulation instrument according to claim 3, wherein the insulating layers are configured as hoses attached onto the inner tube and the outer tube.

5. A bipolar coagulation instrument according to claim 4, wherein the hoses attached onto the inner tube and the outer tube are configured as shrink hoses.

6. A bipolar coagulation instrument according to claim 3, wherein the insulating layers are configured as coatings of a plastic or ceramic material applied onto the inner tube and the outer tube.

7. A bipolar coagulation instrument according to claim 2, wherein the insulating layers are configured as hoses attached onto the inner tube and the outer tube.

8. A bipolar coagulation instrument according to claim 7, wherein the hoses attached onto the inner tube and the outer tube are configured as shrink hoses.

9. A bipolar coagulation instrument according to claim 2, wherein the insulating layers are configured as coatings of a plastic or ceramic material applied onto the inner tube and the outer tube.

10. A bipolar coagulation instrument according to claim 2, wherein the recess surrounding the throttle opening at a distance on all sides is also configured in the insulating layer that coaxially surrounds the outer tube.

11. A bipolar coagulation instrument according to claim 1, wherein the throttle opening is configured in the area of a handle mounted on the proximal end of the shaft.

12. A bipolar coagulation instrument according to claim 1, wherein on the distal ends of the inner tube and of the outer tube, tubular segments protruding in finger-type manner are configured as electrode tips that extend beyond the distal end of the shaft.

13. A bipolar coagulation instrument according to claim 12, wherein the tubular segments protruding like fingers are positioned opposite to one another on the distal end of the shaft.

14. A bipolar coagulation instrument according to claim 13, wherein beveled surfaces, which reduce the outer diameter of the tubes and are inclined diagonally inward, are configured on the distal-side free ends of the tubes at the transition to the protruding electrode tips.

15. A bipolar coagulation instrument according to claim 12, wherein beveled surfaces, which reduce the outer diameter of the tubes and are inclined diagonally inward, are configured on the distal-side free ends of the tubes at the transition to the protruding electrode tips.

* * * * *